United States Patent
Abe et al.

(10) Patent No.: US 6,414,323 B1
(45) Date of Patent: Jul. 2, 2002

(54) CHARGED PARTICLE BEAM APPARATUS AND METHOD OF CONTROLLING CHARGED PARTICLE BEAM

(75) Inventors: Hideaki Abe; Yuuichiro Yamazaki; Motosuke Miyoshi, all of Tokyo-To (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/523,556

(22) Filed: Mar. 10, 2000

(30) Foreign Application Priority Data

Mar. 12, 1999 (JP) ............................................ 11-067221

(51) Int. Cl.⁷ ........................ G01N 21/00; G01N 23/00; G21K 5/08
(52) U.S. Cl. ................. 250/443.1; 250/306; 250/492.1; 250/492.3
(58) Field of Search ........................... 250/492.1, 492.2, 250/492.22, 492.3, 307, 308, 309, 306, 443.1, 440.11, 526

(56) References Cited

U.S. PATENT DOCUMENTS 4,860,224 A * 8/1989 Cashell et al. ......... 364/551.01
5,864,389 A * 1/1999 Osannai et al. ............... 355/53

FOREIGN PATENT DOCUMENTS

JP          5-237304         9/1993

OTHER PUBLICATIONS

H. Abe, et al., Reduction of EB–Induced Contamination in CD–SEM Measurement Using Cold Trap Plate, LSI Testing Symp., Osaka, Japan, pp. 144–149, 1998.

* cited by examiner

Primary Examiner—John R. Lee
Assistant Examiner—David Vanore
(74) Attorney, Agent, or Firm—Finnegan, Henderson, Farabow, Garrett & Dunner, L.L.P.

(57) ABSTRACT

There is here disclosed charged particle beam apparatus in which reactant floating in vacuum can efficiently be removed by simple structure. The charged particle beam apparatus of the present invention comprises a pulse tube refrigerator, a refrigerator controller for controlling the refrigerator, a compressor, a high-pressure rotary valve, a low-pressure rotary valve, and an active damper for removing vibration generated in the refrigerator. Since a cold section is disposed between an objective lens and a specimen in a vacuum container, and adsorbs the reactant in the vacuum container, the amount of reactant in the vacuum container can be reduced, the errors of the critical dimension value of a critical dimension SEM are reduced, and measurement precision is improved. Moreover, since a pulse tube is used as the refrigerator for cooling the cold section, the structure of the apparatus can be simplified and miniaturized. Accordingly, the vibration can be suppressed, and the measurement precision can be enhanced, maintenance can be facilitated, and a running cost can be reduced.

20 Claims, 10 Drawing Sheets

1: COLUMN
2: VACUUM CHAMBER
3: ELECTRON GUN
4: CONDENSER LENS
5: APERTURE
6: OBJECTIVE LENS
7: SECONDARY ELECTRON DETECTOR
8: SPECIMEN
9: SPECIMEN TABLE
10: COLD SECTION

11: REFRIGERATOR
12: THERMOCOUPLE
13: REFRIGERATOR CONTROLLER
14: COMPRESSOR
15: HIGH-PRESSURE ROTARY VALVE
16: LOW-PRESSURE ROTARY VALVE
17: ACTIVE DAMPER
18: DISPLACEMENT/ACCELERATION SENSOR
19: ACTUATOR
20: ACTIVE DAMPER CONTROLLER

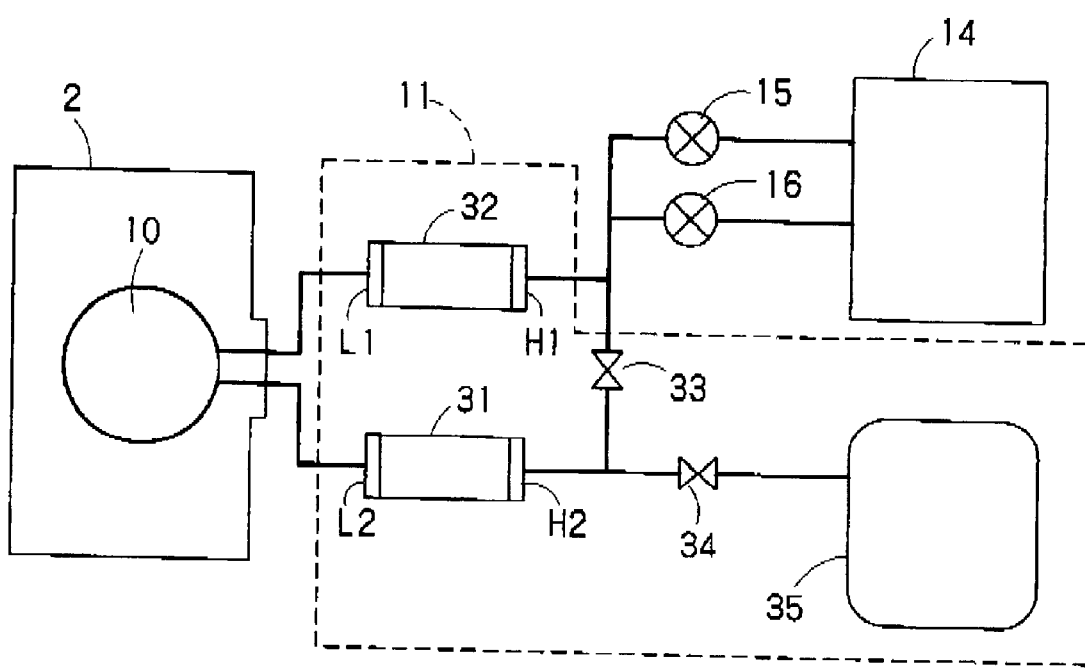
F I G. 2

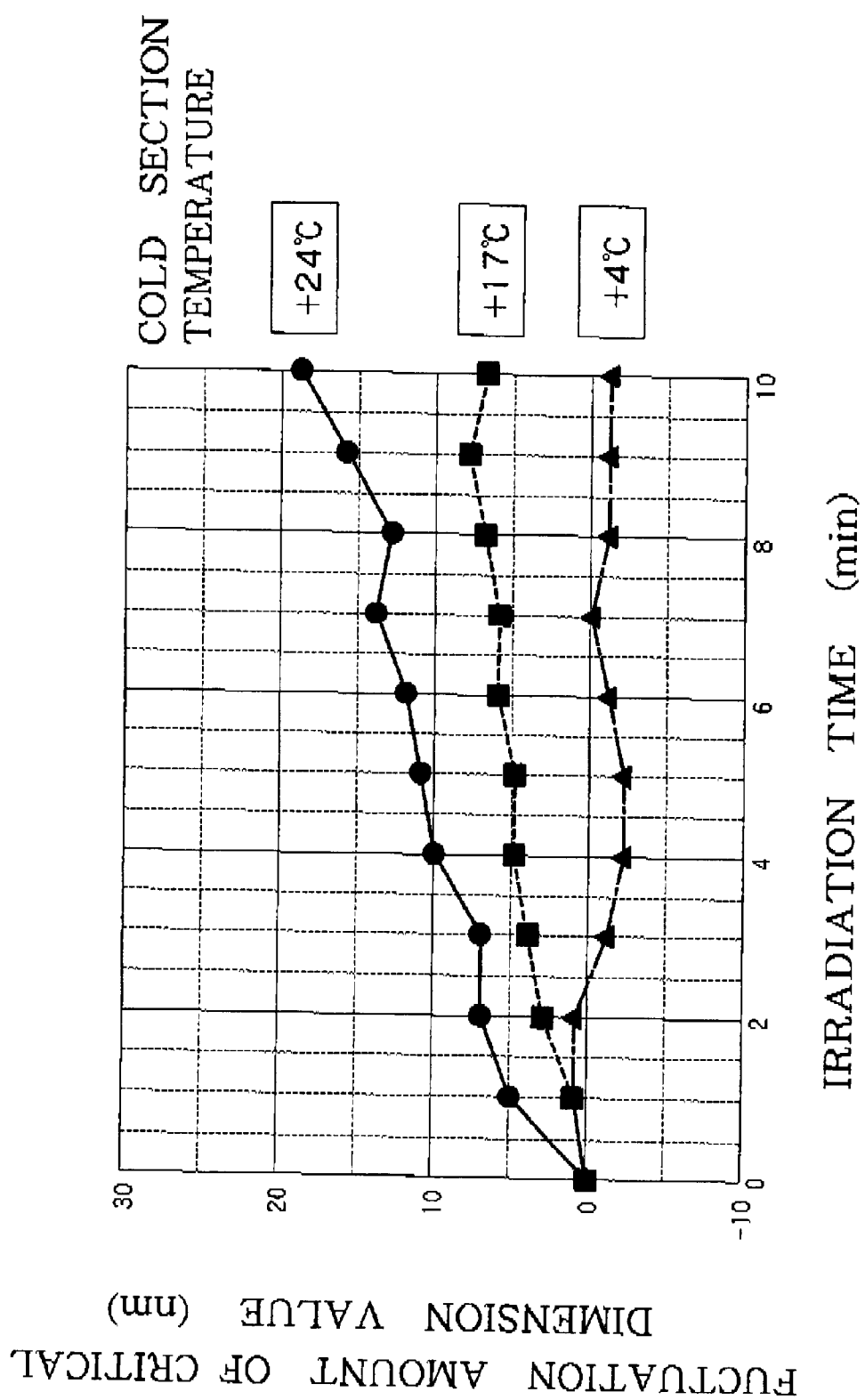
F I G. 6

TEMPERATURE FOR ADSORBING HYDROCARBON (VACUUM DEGREE = $1 \times 10^{-6}$ torr)

| HYDROCARBON NAME | TEMPERATURE (°C) |
|---|---|
| NANODECANE | 11 |
| OCTADECANE | 3 |
| HEPTADECANE | -6 |
| HEXADECANE | -14 |
| PENTADECANE | -24 |
| TETRADECANE | -34 |
| TRIDECANE | -46 |
| DODECANE | -55 |
| UNDECANE | -67 |
| DECANE | -79 |
| NANONE | -91 |
| OCTANE | -105 |
| HEPTANE | -112 |
| HEXANE | -134 |
| PROPYLENE OXIDE | -136 |
| HENTANE | -150 |
| PROPANE | -185 |
| ACETYLENE | -200 |
| ETHANE | -205 |
| ETHYLENE | -210 |
| METHANE | -236 |

FIG. 8

CHARGED PARTICLE BEAM APPARATUS AND METHOD OF CONTROLLING CHARGED PARTICLE BEAM

BACKGROUND OF THE INVENTION

1. Field of the Invention

The present invention relates to charged particle beam apparatus for use in an electron microscope, a critical dimension scanning electron microscopy (SEM), a defect detecting apparatus, charged particle beams exposure apparatus, a focused ion beam (FIB) apparatus, an Auger analysis apparatus, or the like. More particularly, it relates to a technique of reducing contaminants floating in vacuum.

2. Related Background Art

When a specimen is radiated with charged particle beams, the specimen has to be contained in a vacuum container. Because various reactant, however, exist inside the vacuum container, vacuum deterioration and beam-induced contamination is often caused.

When the specimen is placed in the vacuum container, various substances are emitted from the specimen. For example, water and hydrocarbon-based molecules is emitted from a resist coated on a wafer which is used when fine pattern is exposed to light for LSI pattern lithography. These substances are also emitted from not only the resist but also the etched wafer in some cases.

Furthermore, when the specimen is irradiated with the charged particle beams, the charged particle beams reacts with the substances on the surface of the specimen, so that the reactant are emitted into vacuum.

Additionally, there is a possibility that the substances sticking to surface of the specimen while the specimen is exposed to the atmospheric air are emitted into the vacuum container.

The substances emitted from the specimen in this manner float in the vacuum, and further possibly stick to the inner wall of the vacuum container.

Besides the reactant from the above-described specimen, in the vacuum container, there are substances such as an O ring, a vacuum grease, a resin, a wire, and the like which become sources for generating the reactant. Even when the vacuum container is left to stand in the vacuum for a long time, it is impossible to remove the hydrocarbon-based molecules included in the reactant.

As a technique for reducing the reactant which cause the vacuum deterioration and the beam-induced contamination, cooling method using a cold trap has been proposed. The cold trap cools a cooling section disposed in a place where the reactant are to be removed, and allows the cooling section to adsorb the reactant present in the vacuum. In a conventional cooling system utilizing this type of cold trap, the cooling section is cooled by supplying or circulating a cooling material such as liquid nitrogen.

However, in order to constantly keep the cooling temperature of the cooling section, the cooling material has to be constantly refilled, and so a running cost increases. Moreover, to refill the cooling material, a container such as a Dewar vessel or a bomb need to be frequently exchanged, which increases the burden of an operator. Particularly, in the case of a filling type, the temperature of the cooling section rises with the elapse of time, so that the adsorption performance of the reactant decreases by degrees during operation, and it becomes impossible to effectively reduce the reactant. Accordingly, the cooling material needs to be frequently refilled.

Moreover, the above-described conventional cooling system requires peripheral facilities such as the Dewar vessel or the bomb to be filled with the cooling material, a vacuum insulating pipe for guiding the cooling material into the apparatus, a heater for exhausting the used cooling material, and a cabinet for preventing environmental contamination due to dew condensation, so that the system is inconveniently enlarged in scale. Furthermore, when a liquefied substance is used as the cooling material, a temperature response rate of the cooling section is slow, so that it takes a long time until the temperature is stabilized.

For the above-described reasons, it has conventionally been difficult to constantly cool the cooling section and continuously use the cold trap.

SUMMARY OF THE INVENTION

The present invention has been developed in consideration of the above-described respects, and an object of the present invention is to provide charged particle beam apparatus which can efficiently remove reactant floating in vacuum, although constituted by simple structure.

To attain the above-described object, according to the present invention, there is provided charged particle beam apparatus comprising:

an optical mirror cylinder having a lens optical system for focusing charged particle beams from charged particle beam source;

a vacuum container connected to the optical mirror cylinder and containing a specimen beam on which a specimen is put;

a cooling section for adsorbing reactant present in the vacuum container;

an extremely low temperature refrigerator for cooling the cooling section;

an active damper for removing vibration generated in the extremely low temperature refrigerator; and an active damper control section for controlling the active damper.

Moreover, according to the present invention, there is provided charged particle beam apparatus comprising:

an optical mirror cylinder having a lens optical system for focusing charged particle beams from charged particle beam source;

a vacuum container connected to the optical mirror cylinder and containing a specimen base on which a specimen is put;

a cooling section for adsorbing reactant present in the vacuum container; and an extremely low temperature refrigerator for cooling the cooling section, wherein the extremely low temperature refrigerator has a pulse tube for containing a gas which behaves in the same way as piston movement by using pressure vibration, and cools the cooling section by expansion of the gas in the pulse tube.

According to the present invention, the cooling section is disposed to adsorb the reactant present in the vacuum container, and the vibration generated in the extremely low temperature refrigerator is removed by the active damper, so that the deviation of the charged particle beams can be suppressed.

Moreover, the vibration amount can further be suppressed by using the extremely low temperature refrigerator of a pulse tube type.

Furthermore, by fixing the reference temperature of the cooling section in accordance with the reactant present in the vacuum container, the reactant can efficiently be adsorbed in the cooling section.

Additionally, by disposing the cooling sections on a plurality of places in the optical mirror cylinder and the vacuum container, vacuum degree can further be enhanced.

BRIEF DESCRIPTION OF THE DRAWINGS

FIG. 2 is a block diagram showing the detailed constitution of a refrigerator.

FIG. 6 is a diagram showing a relation between the irradiation time of charged particle beams and the fluctuation amount of a critical dimension value.

FIG. 8 is a diagram showing a relation between the hydrocarbon name and the adsorption temperature.

DETAILED DESCRIPTION OF THE PREFERRED EMBODIMENTS

The charged particle beam apparatus of the present invention will specifically be described hereinafter with reference to the drawings. In the following, an example in which the charged particle beam apparatus is applied to a critical dimension SEM will be described mainly.

(First Embodiment)

Figure 1:
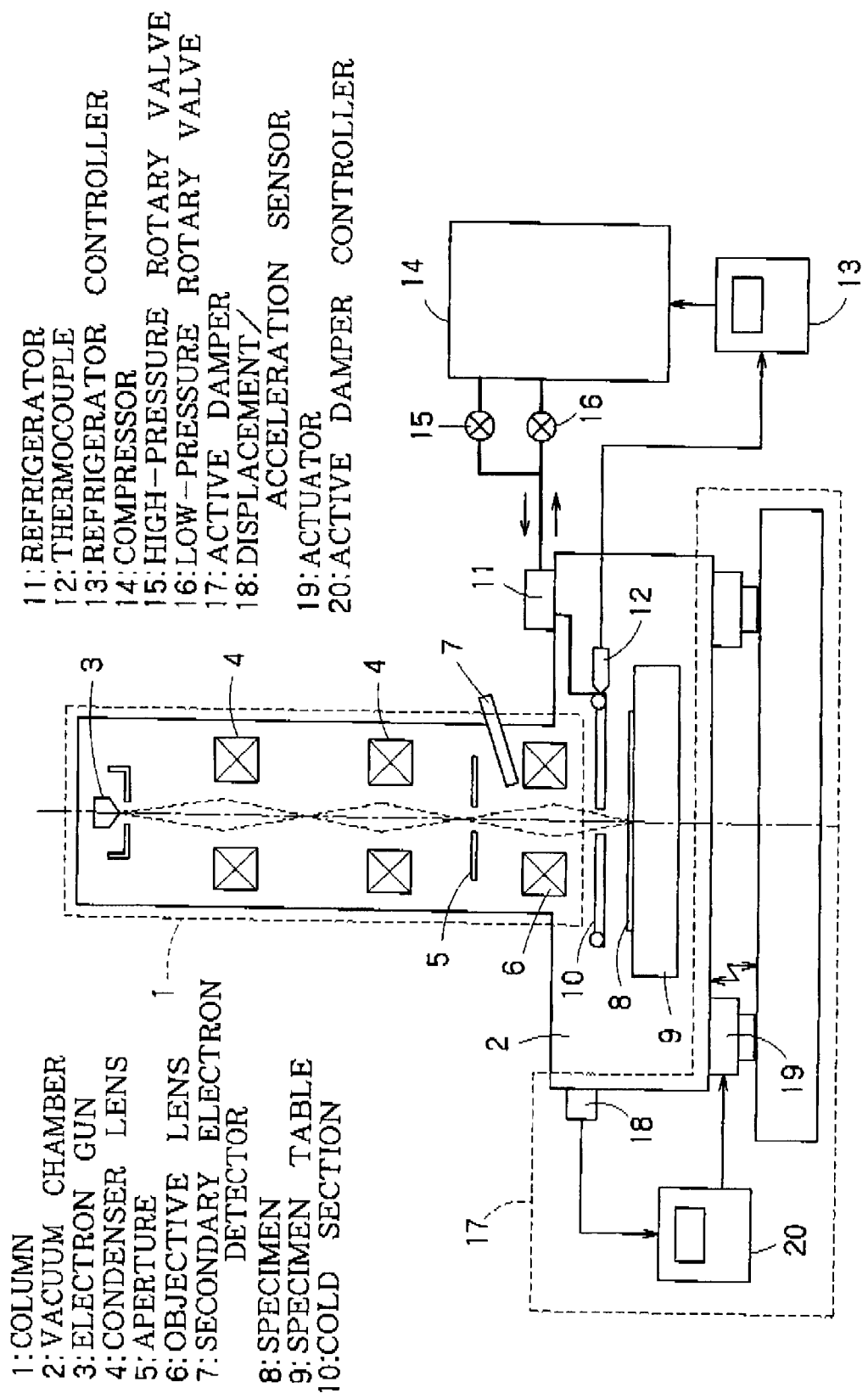
FIG. 1 is a block diagram showing the schematic configuration of a critical dimension SEM according to a first embodiment.

FIG. 1 is a block diagram showing the schematic configuration of the critical dimension SEM according to a first embodiment. The critical dimension SEM of FIG. 1 is provided with an optical mirror cylinder 1 and a vacuum container 2. In the optical mirror cylinder 1, an electron gun 3, a condenser lens 4, a diaphragm 5, an objective lens 6, and a secondary electron detector 7 are disposed. In the vacuum container 2, a specimen base 9 on which a specimen 8 is put, a cold section 10 and a refrigerator 11 described later, an a thermocouple 12 are disposed.

Moreover, the critical dimension SEM of FIG. 1 includes a refrigerator controller 13 for controlling the refrigerator 11, a compressor 14, a high-pressure rotary valve 15, a low-pressure rotary valve 16, and an active damper 17 for removing the vibration generated in the refrigerator 11.

In the critical dimension SEM of FIG. 1, the electron beam emitted from the electron gun 3 is focused by the condenser lens 4, and then formed into a beam shape with a desired size by the diaphragm 5. The electron beam passed through the diaphragm 5 is focused by the objective lens 6, and is then irradiated at a desired position on the specimen 8. The secondary electron emitted from the specimen 8 is detected by the secondary electron detector 7.

The cold section 10 of FIG. 1 is disposed in the vicinity of the specimen 8 in the vacuum container 2, and adsorbs the reactant floating in the vicinity of the path of the electron beam. Examples of the reactant present in the vacuum container 2 include water and hydrocarbon-based molecules emitted from the inner wall of the vacuum container 2 and the specimen 8, air (oxygen and nitrogen) flowing in from the outside by a leak, and the like.

FIG. 2 is a view for explaining the cooling principle of the cold section 10. The present embodiment is characterized in the use of the pulse tube refrigerator 11. Specifically, as shown in FIG. 2, the refrigerator 11 of the present embodiment includes a pulse tube 31 containing a gas which behave in the same way as the piston movement by using pressure vibration, a cold accumulator 32, channel resistors 33 and 34, and a reservoir 35.

The reservoir 35 is held to provide a substantially constant pressure by means of the channel resistor 34. Pipings in which cooling material such as a helium gas is sealed are attached to the outer face of the cold section 10, and the cold section 10 is connected to low-temperature ends L1 and L2 of the cold accumulator 32 and pulse tube 31 via the piping.

Since the gas in the pulse tube 31 behaves in the same way as the piston movement in accordance with the opening/closing of the high-pressure rotary valve 15 and low-pressure rotary valve 16, it is called a gas piston. The cold section 10 of FIG. 2 carries out cooling by using the gas piston.

Figure 3:
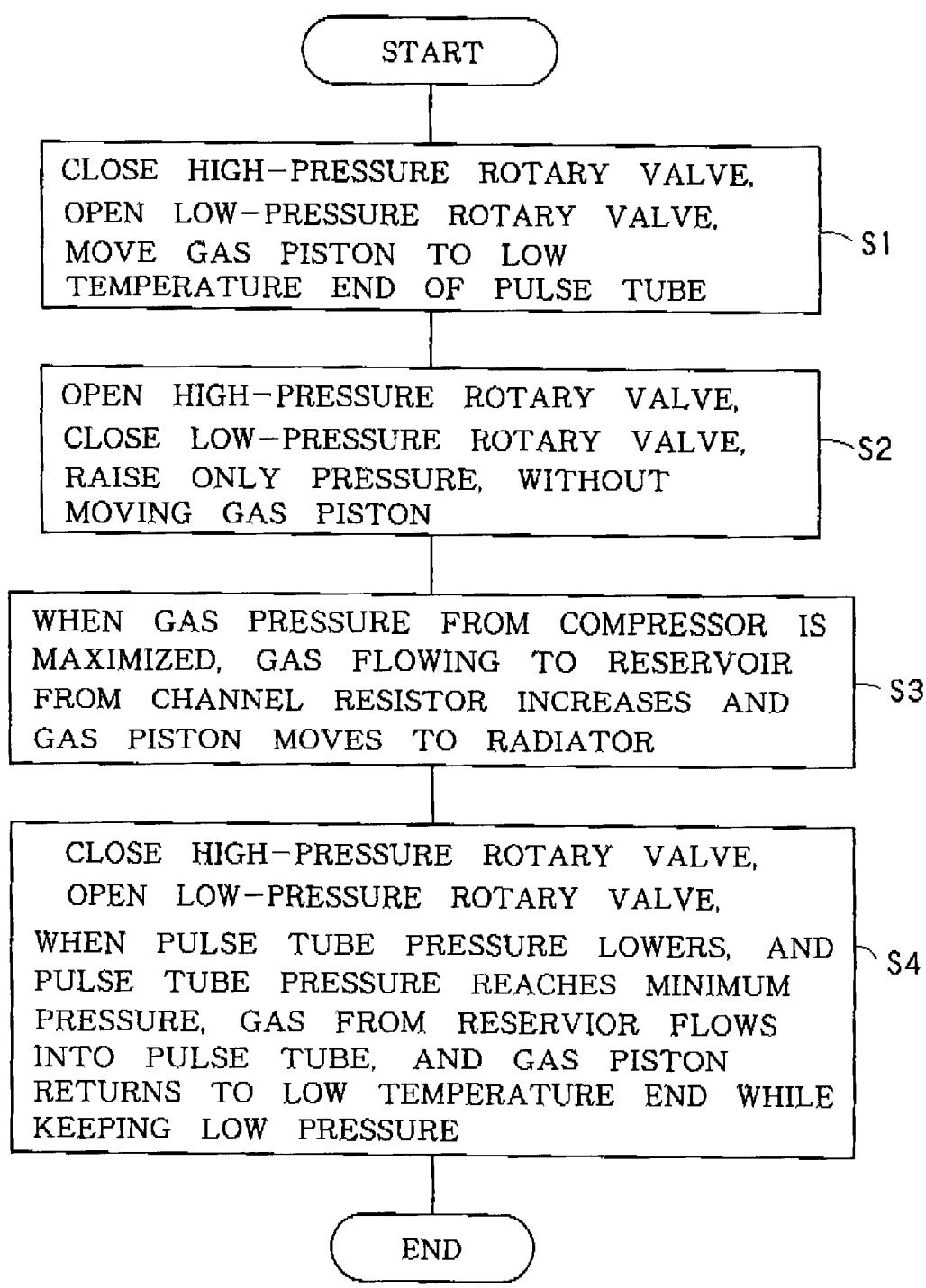
FIG. 3 is a flowchart showing the cooling process of the cold section of FIG. 2.

FIG. 3 is a flowchart showing the cooling process of the cold section 10 of FIG. 2, and the cooling process of the cold section 10 will be described hereinafter in order based on the flowchart. First, when the high-pressure rotary valve 15 is closed, and the low-pressure rotary valve 16 is opened, the pressure in the system is substantially low, and the gas piston is positioned in the low-temperature end L2 of the pulse tube 31 (step S1).

Subsequently, when the low-pressure rotary valve 16 is closed and the high-pressure rotary valve 15 is opened, the high-pressure gas flows into the pulse tube 31 via the cold accumulator 32, and tries to push the gas piston toward a radiator H2. However, since the high-pressure gas flows in via the channel resistor 33 from the radiator, the gas piston does not move, and only the gas pressure rises (step S2).

Next, when the gas pressure from the compressor 14 reaches its maximum, the gas flowing to the reservoir 35 from the channel resistor 34 increases and the gas piston moves toward the radiator H2 (step S3). In this case, the volume inside the pulse tube 31 expands and the pressure of the pulse tube 31 lowers.

Subsequently, when the high-pressure rotary valve 15 is closed and the low-pressure rotary valve 16 is opened, the pressure inside the pulse tube 31 further lowers (step S4).

When the pressure of the pulse tube 31 reaches the minimum pressure, the gas from the reservoir 35 flows into the pulse tube 31, and the gas piston returns to the low-temperature end L2 while keeping substantially the low pressure.

As described above, the low-temperature end L1 of the cold accumulator 32 and the cold section 10 are cooled by the expansion process of the gas piston.

The cold section 10 in the critical dimension SEM of FIG. 1 is cooled by the refrigerator 11 attached to the outside of the vacuum container 2 in the same principle as that of FIG. 2. Moreover, the cold section 10 of FIG. 1 is disposed between the specimen 8 and the objective lens 6, and has a thin disc-shaped electrode, which is, for example, formed by using materials such as BeCu. Furthermore, in order to efficiently reduce the reactant in the vicinity of the path of the electron beam, the cold section 10 is disposed as close to the specimen 8 as possible right above the specimen 8.

The cold section 10 is thermally and electrically insulated from the objective lens 6, and the beam axis deviation by cooling is accordingly prevented. The temperature of the cold section 10 is constantly measured by the thermocouple 12, and the refrigerator controller 13 calculates a temperature difference between the temperature of the cold section 10 and a predetermined temperature. When the temperature difference deviates from a prescribed range, the refrigerator controller 13 automatically adjusts the change-over frequency and the gas pressure of the high-pressure rotary valve 15 and the low-pressure rotary valve 16 in order to control the temperature of the cold section 10.

The temperature of the cold section 10 is kept to be constant by the feedback control. Moreover, by repeating the process of steps S1 to S4 of FIG. 3, it is possible to carry out the cooling approximately until a liquid helium temperature.

In the critical dimension SEM of FIG. 1, during the cooling, the vibration is generated by the operation of the compressor 14, high-pressure rotary valve 15, and low-pressure rotary valve 16, and there is a possibility that the performances such as resolution are deteriorated by the vibration. Therefore, the vibration is suppressed by the active damper 17.

The active damper 17 is constituted of a displacement/acceleration sensor 18 for detecting the vibration generated in the vacuum container 2, an actuator 19 for moving the vacuum container 2 in a direction in which the vibration is canceled, and an active damper controller 20 for controlling drive of the actuator 19.

The displacement/acceleration sensor 18 is attached, for example, to the vacuum container 2 to constantly detect the vibration of the vacuum container 2 and to transmit the detected signal to the active damper controller 20. The active damper controller 20 carries out calculation to suppress the vibration and drives/controls the actuator 19. The vibration of the vacuum container 2 during cooling is suppressed by such a feedback control, and the apparatus is stabilized.

Additionally, the electron gun 3 of FIG. 1 corresponds to the charged particle beam source, the capacitor 4, diaphragm 5 and objective lens 6 correspond to the deflecting means, the refrigerator 11 corresponds to the extremely low temperature refrigerator, the thermocouple 12 corresponds to the temperature measuring section, and the refrigerator controller 13 corresponds to the temperature adjusting section.

Figure 4:
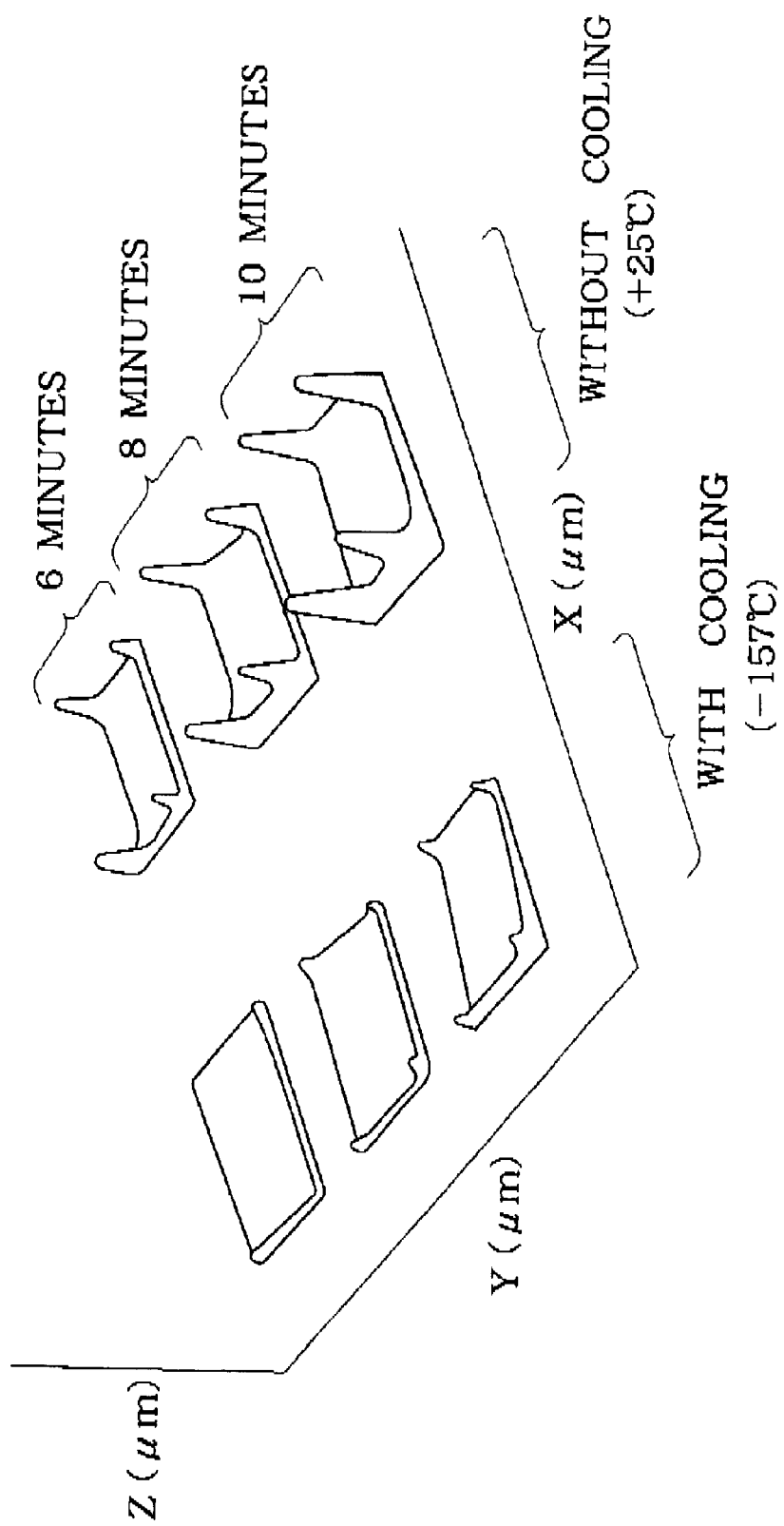
FIG. 4 is a diagram of a three-dimensional AFM image showing a result comparing the deposition amounts of electron beam-induced contamination in the cases that the cold section is disposed and is not disposed.

FIG. 4 is a diagram showing a three-dimensional AFM image comparing the deposition amounts of beam-induced contamination with cooling and without cooling. In FIG. 4, X-axis and Y-axis show the two-dimensional coordinate of the surface of the specimen 8, and Z-axis shows the deposition amount. FIG. 4 shows the AFM image for the electron beam-induced time of six, eight, and ten minutes with the cold section 10 and without any cold section.

The deposits by the electron beam irradiation are mainly hydrocarbon-based molecules polymerized/deposited by the electron beam irradiation, and particularly main generating sources include, for example, hydrocarbon-based molecules floating in vacuum, hydrocarbon-based molecules emitted from the specimen in the vacuum, and hydrocarbon-based molecules forcibly emitted from the specimen by the electron beam irradiation.

As seen from FIG. 4, by disposing the cold section 10, the reactant represented by the hydrocarbon-based molecules are efficiently adsorbed by the cold section, and the deposition amounts of the corner and central parts of the irradiation area decrease.

Figure 5:
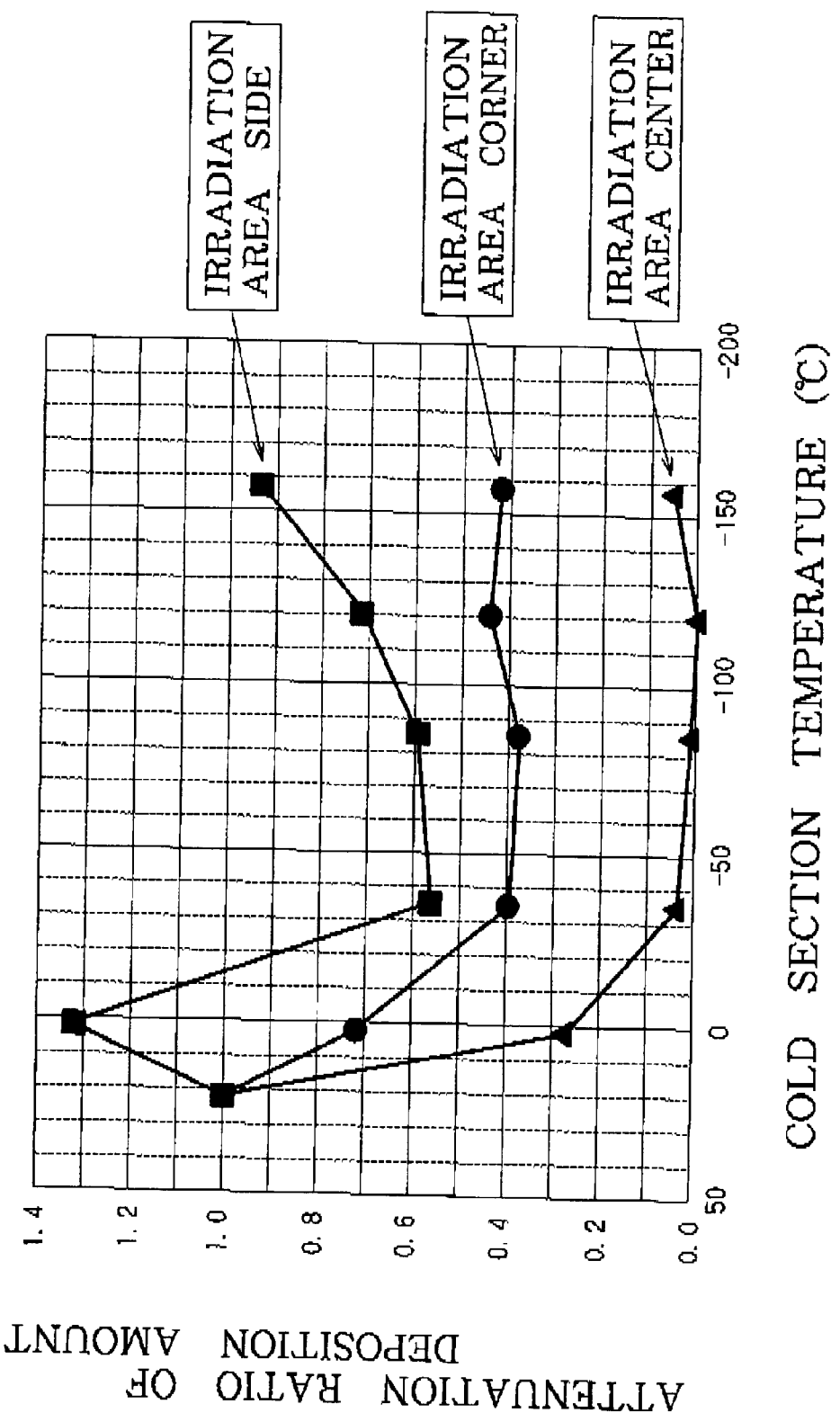
FIG. 5 is a diagram showing a relation between the temperature of a cold section and reduction ratio of the deposition amount in respective irradiation area parts.

On the other hand, FIG. 5 is a diagram showing a relation between the temperature of the cold section 10 and reduction ratio of the decomposition amount in each irradiation area part. As shown in FIG. 5, when the temperature of the cold section 10 equals to or is less than $-30°$ C., the deposition amount attenuation ratios of the irradiation area corner and central parts become substantially constant. Additionally, when the temperature of the irradiation area side part equals to or is less than $-100°$ C., the deposition attenuation ratio is deteriorated. This is supposedly because the reactant on the specimen surface become more dominant than the reactant in the vacuum container.

Moreover, FIG. 6 is a diagram showing the relation between the electron beam-induced time and fluctuation amount of the critical dimension value with respect to the respective temperatures of the cold section 10 of $24°$ C., $17°$ C. and $4°$ C. As shown in FIG. 6, when the temperature of the cold section 10 equals to or is less than $4°$ C., the deposition amount decreases, and it is seen that the critical dimension value hardly fluctuates.

As described above, in the first embodiment, the cold section 10 is disposed between the objective lens 6 and the specimen 8 in the vacuum container 2, and the cold section 10 adsorbs the reactant in the vacuum container 2. Because of this, the amount of the reactant in the vacuum container 2 can be decreased, the critical dimension value errors of the critical dimension SEM are reduced, and the measurement precision is improved.

Moreover, since the pulse tube is used as the refrigerator 11 for cooling the cold section 10, the structure can be simplified and miniaturized. Additionally, since the vibration is minimized, the measurement precision is enhanced, maintenance is facilitated, and the running cost can be reduced.

Furthermore, since the active damper 17 is disposed to suppress the vibration generated by the compressor 14 and the like, the beam deviation or the like by the vibration can be suppressed.

(Second Embodiment)

The optimum temperature of the cold section 10 necessary for the adsorption differs with the types of the reactant. Therefore, in the following described second embodiment, the temperature of the cold section 10 is automatically adjusted based on a result analyzing the types of the reactant.

Figure 7:
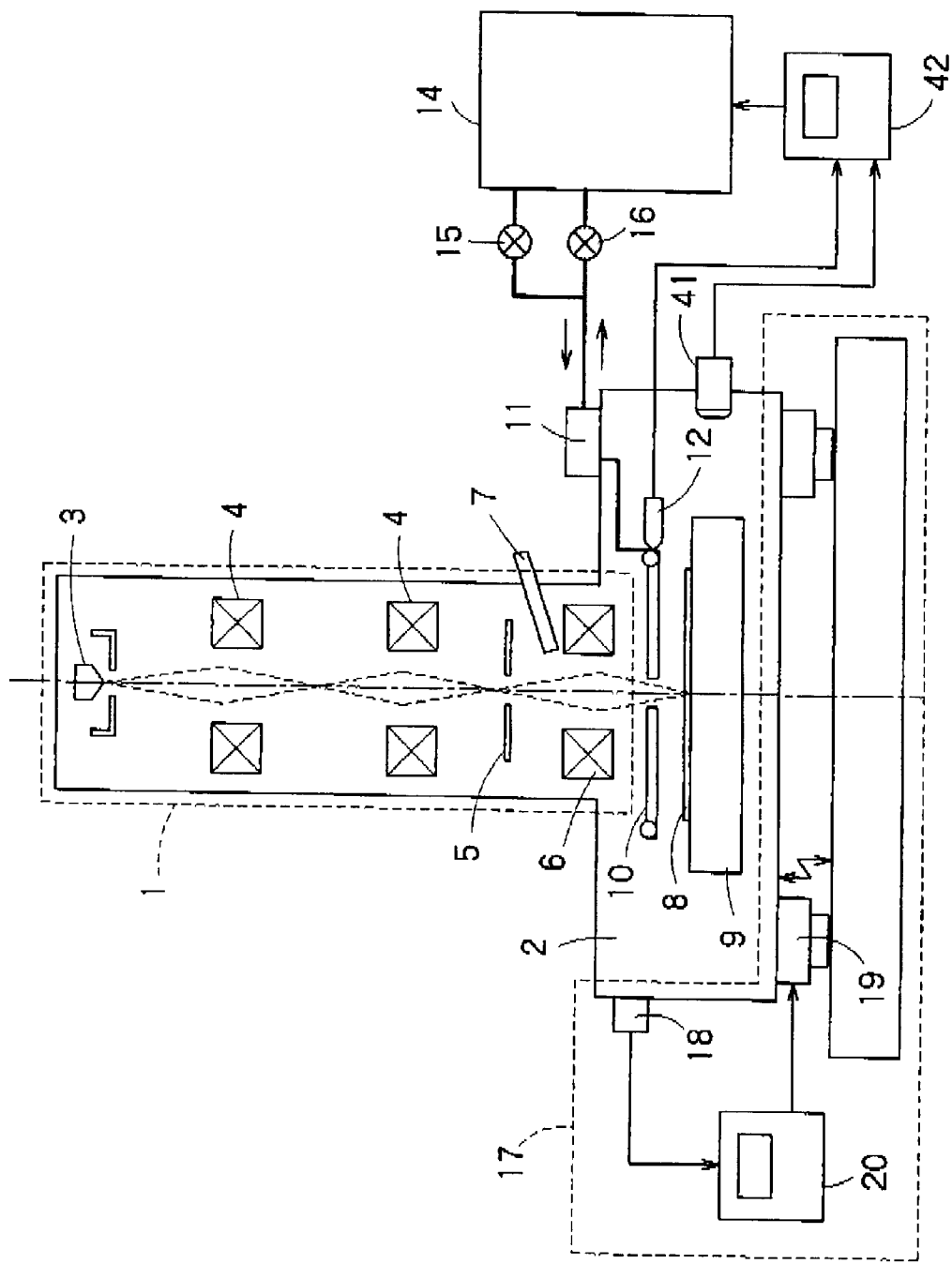
FIG. 7 is a block diagram showing the schematic configuration of the critical dimension SEM according to a second embodiment.

FIG. 7 is a block diagram showing the schematic configuration of the critical dimension SEM according to the second embodiment. In FIG. 7, the constituting parts common to those of FIG. 1 are denoted with the same reference numerals, and mainly the different respects will be described hereinafter.

The critical dimension SEM of FIG. 7 is provided with a gas analyzer (analyzing section) 41 constituted of a mass analysis meter for analyzing the atmosphere in the vacuum container 2, and a temperature setter (reference temperature setting section) 42 for setting the reference cooling temperature of the cold section 10 based on the result analyzed by the analyzer 41. Additionally, in the embodiment shown in FIG. 7, the temperature setter 42 also functions as the refrigerator controller 13 of FIG. 1, but they may separately be disposed.

The hydrocarbon-based molecules causing the beam-induced contamination differ in the cooling temperature at which they can adsorbed in the cold section 10. FIG. 8 is a chart showing a relation between hydrocarbon names and adsorption temperatures. As shown in FIG. 8, the adsorption temperature differs in accordance with the hydrocarbon types.

Therefore, when the gas analyzer 41 detects the hydrocarbon-based molecules, the cooling temperature necessary for the adsorption is calculated from the molecular weight, an control signal is transmitted to the refrigerator controller 13, in order to constantly set the optimum cooling temperature.

As described above, in the second embodiment, since the cooling temperature of the cold section 10 is set in accordance with the types of the reactant present in the vacuum container 2, the reactant are efficiently adsorbed by the cold section 10, and excess cooling can be avoided.

(Third Embodiment)

In a third embodiment, by disposing the cold sections 10 on a plurality of places in the optical mirror cylinder 1 and the vacuum container 2, the vacuum degree is raised.

Figure 9:
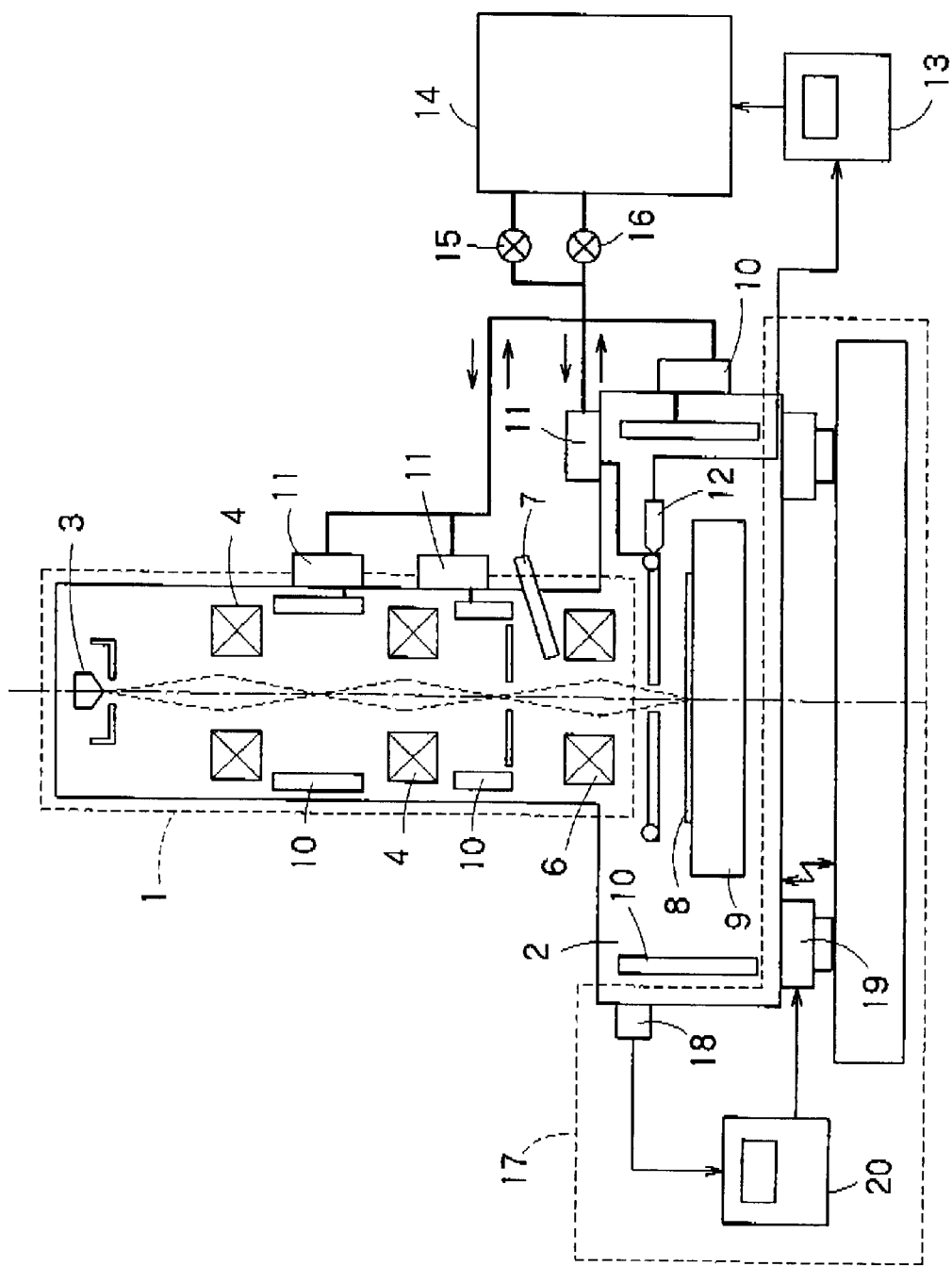
FIG. 9 is a block diagram showing the schematic configuration of the critical dimension SEM according to a third embodiment.

FIG. 9 is a block diagram showing the schematic configuration of the critical dimension SEM according to the third embodiment. In FIG. 9, the constituents common to those of FIG. 1 are denoted with the same reference numerals, and mainly the different respects will be described hereinafter.

The cold section 10 of the third embodiment is disposed not only between the objective lens 6 and the specimen base 9 but also between two condenser lenses 4, between the condenser lens 4 and the diaphragm 5, and on the outer wall of the vacuum container 2.

Thus, by disposing the cold sections 10 on a plurality of places in the optical mirror cylinder 1 and vacuum container 2, the absolute amount of reactant can be reduced, and the vacuum degree of the entire apparatus can be enhanced. Therefore, no reactant is attached/deposited onto the optical mirror cylinder components, and the charged particle beam apparatus can be stabilized.

Additionally, the places where the cold section 10 is to be disposed and the number of cold sections 10 are not limited to those shown in FIG. 9, but the cold section is preferably disposed in the vicinity of the electron beam path.

(Fourth Embodiment)

In the first to third embodiments, the examples have been described in which the active damper 17 is used to offset the vibration by the compressor 14 and the like, but the active damper 17 may be omitted because the pulse tube refrigerator 11 originally has little vibration.

Figure 10:
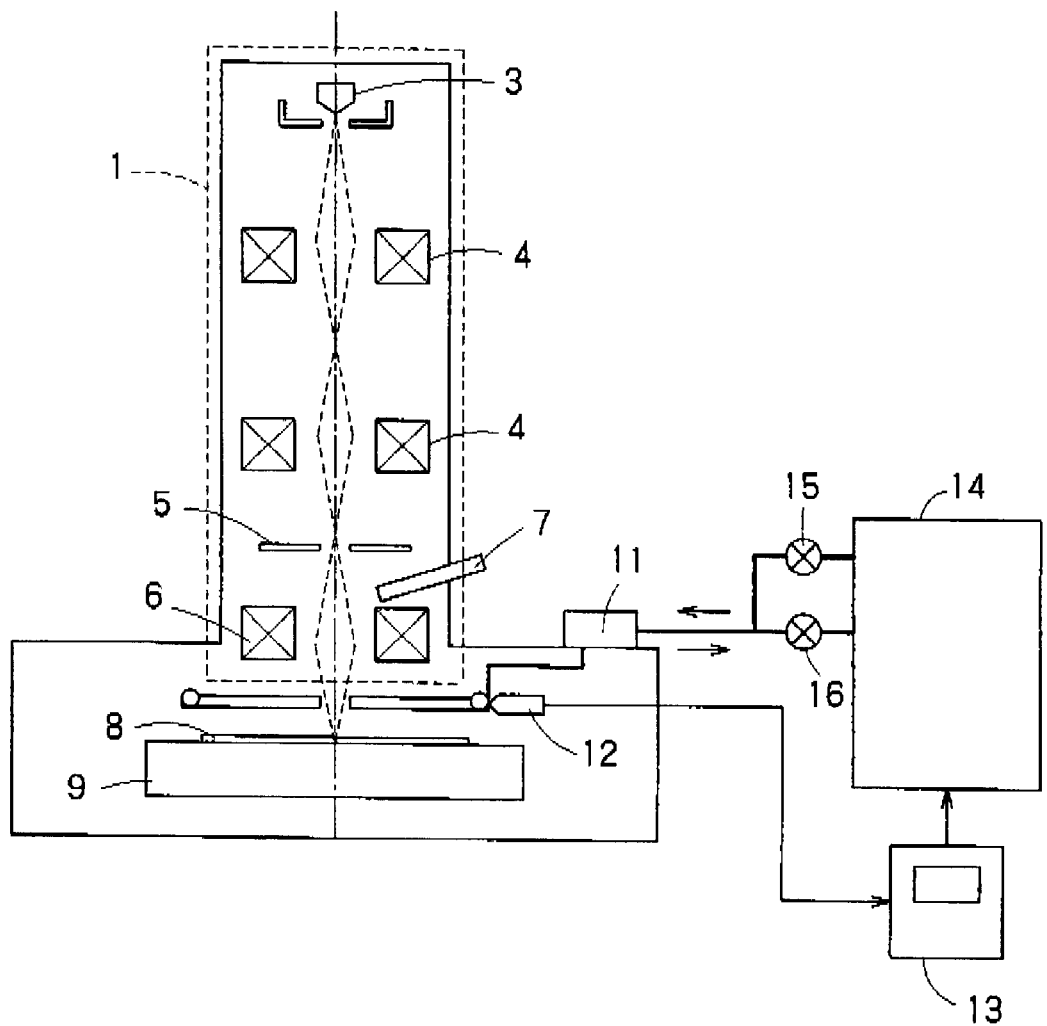
FIG. 10 is a block diagram showing the schematic configuration of the critical dimension SEM according to a fourth embodiment.

FIG. 10 is a block diagram showing the schematic configuration of the critical dimension SEM according to a fourth embodiment. The critical dimension SEM of FIG. 10 is constituted in the same way as that of FIG. 1, except that the active damper 17 is omitted. By omitting the active damper 17, the constitution can be simplified and miniaturized, and the cost can be reduced.

Additionally, in the first to fourth embodiments, the examples of the use of the pulse tube refrigerator 11 have been described, but the refrigerator 11 other than the pulse tube may be used. The refrigerator 11 other than the pulse tube more easily generates the vibration than the pulse tube refrigerator 11, but by disposing the active damper 17 shown in FIG. 1, the vibration can be offset, so that the electron beam deviation can be suppressed.

Moreover, the example in which the temperature of the cold section 10 is measured by the thermocouple 12 and the measured temperature is feedback-controlled has been described with reference to FIG. 1 and the like, but when precision is not so much required, the feedback control of the temperature may be omitted.

In the above-described embodiments, the critical dimension SEM has been described as an example, but the present invention can broadly be applied to various apparatuses utilizing the charged particle beams, such as an electron microscope, a defect check apparatus, an exposure apparatus, FIB, an Auger analysis apparatus.

What is claimed is:

1. A charged particle beam apparatus comprising:
   an optical mirror cylinder having a lens optical system for focusing charged particle beams from charged particle beam source;
   a vacuum container connected to said optical mirror cylinder and containing a specimen base on which a specimen is put;
   a cooling section for adsorbing reactant present in said vacuum container;
   an extremely low temperature refrigerator for cooling said cooling section;
   an active damper for removing vibration generated in said extremely low temperature refrigerator; and
   an active damper control section for controlling said active damper.

2. The charged particle beam apparatus according to claim 1 wherein said cooling section is disposed on a side closer to the specimen between said lens optical system and the specimen.

3. The charged particle beam apparatus according to claim 1, further comprising deflecting means for irradiating a desired position on specimen surface with the charged particle beams, of for scanning the charged particle beams in a desired area on the specimen surface,
   said deflecting means being contained in said optical mirror cylinder.

4. The charged particle beam apparatus according to claim 1, further comprising:
   a temperature measuring section for measuring the temperature of said cooling section; and
   a temperature adjusting section for adjusting the temperature of said cooling section so that the measured temperature reaches a predetermined reference temperature.

5. The charged particle beam apparatus according to claim 4, further comprising:
   an analyzing section for analyzing types of reactant present in said vacuum container; and
   a reference temperature setting section for setting the reference temperature to be optimum in accordance with the reactant present in said vacuum container, based on a result analyzed by said analyzing section.

6. The charged particle beam apparatus according to claim 1 wherein said cooling sections are disposed on a plurality of locations in said optical mirror cylinder and said vacuum container.

7. The charged particle beam apparatus comprising:
   an optical mirror cylinder having a lens optical system for focusing charged particle beams from charged particle beam source;

a vacuum container connected to said optical mirror cylinder and containing a specimen base on which a specimen is put;

a cooling section for adsorbing reactant present in said vacuum container; and an extremely low temperature refrigerator for cooling said cooling section, wherein said extremely low temperature refrigerator has a pulse tube for containing a gas which behaves in the same way as piston movement by using pressure vibration, and cools said cooling section by the expansion of the gas in said pulse tube.

8. The charged particle beam apparatus according to claim 7 wherein said cooling section is disposed on a side closer to the specimen between said lens optical system and the specimen.

9. The charged particle beam apparatus according to claim 7, further comprising deflecting means for irradiating a desired location on specimen surface with the charged particle beams, or for scanning the charged particle beams in a desired area on the specimen surface, said deflecting means being contained in said optical mirror cylinder.

10. The charged particle beam apparatus according to claim 7, further comprising:

an active damper for removing vibration generated in said extremely low temperature refrigerator; and an active damper control section for controlling said active damper.

11. The charged particle beam apparatus according to claim 7, further comprising:

a temperature measuring section for measuring the temperature of said cooling section; and a temperature adjusting section for adjusting the temperature of said cooling section so that the measured temperature reaches a predetermined reference temperature.

12. The charged particle beam apparatus according to claim 11, further comprising:

an analyzing section for analyzing types of reactant present in said vacuum container; and a reference temperature setting section for setting the reference temperature to be optimum in accordance with the reactant present in said vacuum container, based on a result analyzed by said analyzing section.

13. The charged particle beam apparatus according to claim 7 wherein said cooling sections are disposed in a plurality of places in said optical mirror cylinder and said vacuum container.

14. A method of controlling charged particle beam apparatus comprising an optical mirror cylinder having a lens optical system for focusing charged particle beams from a charged particle beam source, and a vacuum container connected to said optical mirror cylinder and containing a specimen base on which a specimen is put; said method comprising the steps of:

allowing a cooling section cooled by an extremely low temperature refrigerator to adsorb reactant present in said vacuum container; and removing vibration generated in said extremely low temperature refrigerator by an active damper.

15. The method of controlling the charged particle beam apparatus according to claim 14, further comprising the steps of:

measuring the temperature of said cooling section, and adjusting the temperature of said cooling section so that the measured temperature reaches a predetermined reference temperature.

16. The method of controlling the charged particle beam apparatus according to claim 15, further comprising the steps of:

analyzing types of reactant present in said vacuum container, and setting the reference temperature to be optimum in accordance with the reactant present in said vacuum container, based on the analyzed result.

17. A method of controlling charged particle beam apparatus comprising an optical mirror cylinder having a lens optical system for focusing charged particle beams from charged particle beam source, and a vacuum container connected to said optical mirror cylinder and containing a specimen base on which a specimen is put;

said method comprising the steps of:

disposing, in said optical mirror cylinder or in said vacuum container, a cooling section comprising a pulse tube for containing a gas which behaves in the same way as piston vibration by using pressure vibration; and cooling said cooling section by the expansion of the gas in said pulse tube, in order to allow said cooling section to adsorb reactant present in said vacuum container.

18. The method of controlling the charged particle beam apparatus according to claim 17, further comprising the steps of:

adjusting pressure is said pulse tube by an extremely low temperature refrigerator to cool said cooling section, and allowing said cooling section to adsorb the reactant present in said vacuum container; and removing vibration generated in said extremely low temperature refrigerator by an active damper.

19. The method of controlling the charged particle beam apparatus according to claim 18, further comprising the steps of:

measuring the temperature of said cooling section, and adjusting the temperature of said cooling section so that the measured temperature reaches a predetermined reference temperature.

20. The method of controlling the charged particle beam apparatus according to claim 19, further comprising the steps of:

analyzing types of reactant present in said vacuum container, and setting the reference temperature to be optimum in accordance with the reactant present in said vacuum container based on an analyzed result.

* * * * *